United States Patent [19]

Enge

[11] Patent Number: 5,451,790

[45] Date of Patent: Sep. 19, 1995

[54] METHOD OF TREATING WASTE OR DRINKING WATER WITH HIGH-ENERGY ELECTRONS AND APPARATUS THEREFOR

[75] Inventor: Harald A. Enge, Lincoln, Mass.

[73] Assignee: Ion Physics Corporation, Atkinson, N.H.

[21] Appl. No.: 184,600

[22] Filed: Jan. 21, 1994

[51] Int. Cl.6 .............................................. G01N 23/12
[52] U.S. Cl. .................... 250/436; 250/432 R; 250/435
[58] Field of Search ............ 250/436, 435, 434, 432 R, 250/437, 492.3, 398; 210/748

[56] References Cited

U.S. PATENT DOCUMENTS

| | | | |
|---|---|---|---|
| 3,988,588 | 10/1976 | Offermann | 250/492.3 |
| 4,230,947 | 10/1980 | Cram | 250/434 |
| 5,072,124 | 12/1991 | Kondo et al. | 250/436 |

*Primary Examiner*—Paul M. Dzierzynski
*Assistant Examiner*—Kiet T. Nguyen
*Attorney, Agent, or Firm*—Nields & Lemack

[57] ABSTRACT

In apparatus for irradiating fluid material with an electron beam, a tubular or circular flow is imparted to the fluid material to be irradiated while a rotary motion is imparted to the electron beam, so that the point of intersection between the electron beam and the fluid material repeatedly moves around a circle through which the material passes.

12 Claims, 5 Drawing Sheets

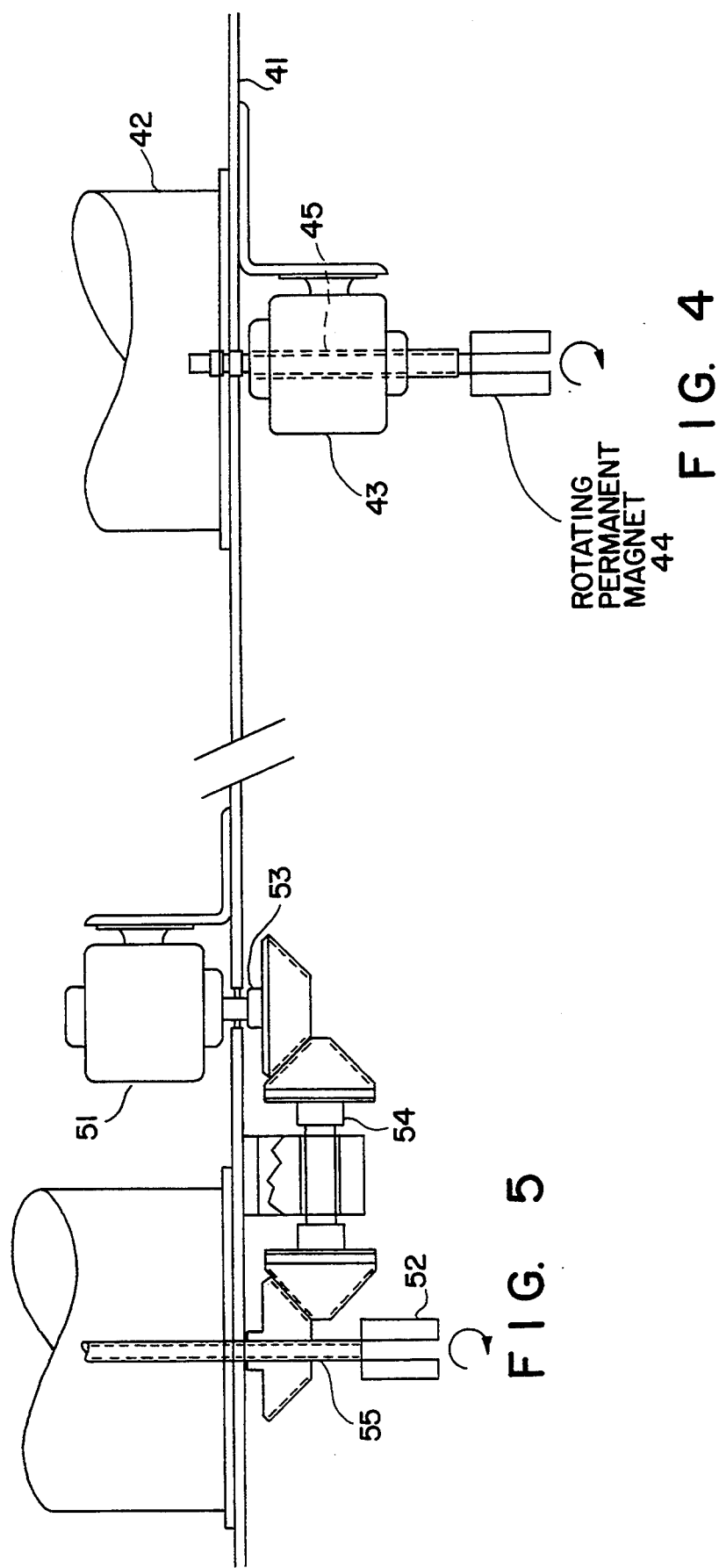

METHOD OF TREATING WASTE OR DRINKING WATER WITH HIGH-ENERGY ELECTRONS AND APPARATUS THEREFOR

BACKGROUND OF THE INVENTION

1. Field of the Invention

The present invention relates to the irradiation of materials in liquid or gaseous form, and in particular to the irradiation of wastes or drinking water with high-energy electrons.

2. Description of the Prior Art

High-energy electron beams are being used in many industrial processes and for sterilization of materials such as surgical equipment and some food products. A new area of application of electron beams is the treatment of gaseous or liquid wastes, not only for sterilization, but also to break up toxic or otherwise undesirable components. Electron irradiation techniques can also be applied to sterilization of drinking water. In the case of gaseous wastes the gas may pass through a "curtain" of electrons formed by scanning the pencil-thin beam emerging from an accelerator rapidly with an oscillating magnetic or electric field. Alternatively, the beam may be sufficiently spread out by scattering in the gas to cover the cross section of a smoke stack.

The order-of-magnitude of the electron energy required for the aforementioned applications of electron irradiation is determined by the nature of the material irradiated. Since the range of 500 keV electrons in air is approximately 1.5 meters, irradiation of the aforementioned gaseous materials may be accomplished with electrons having an energy on the order of 500 keV. Since the range of 2-MeV electrons in water is about 9.5 millimeters, water may be treated with electrons having an energy on the order of 2-MeV if a relatively shallow river or thin waterfall is formed. For this system to be practical it is necessary (a) that the electron beam be very intense (hundreds of milliamperes), and (b) that it can be scanned rapidly across a relatively wide area.

The beam can be scanned in vacuum as it is emerging from the accelerator and thereafter can be made to pass through a thin metallic window, or it can be directed through a small orifice into air or partial vacuum to be scanned immediately thereafter. Multiple scattering by air molecules causes the beam to increase in diameter quite rapidly in air at atmospheric pressure, and so it is important that the scanning mechanism be relatively close to the orifice of emergence. Clearly, the vacuum system has to have several stages of differential pumping between the aforementioned orifice and the high vacuum accelerator section for the electrons. This technique is well known and utilized in electron-beam welding equipment.

For high-volume processes, such as the treatment of waste water or drinking water, a major limitation is that of the water flow, which must be uniform and fast. The need for high flow rates may be seen from the following analysis, which shows that the specific treatment costs ($/gallon) are significantly reduced if the facility treats larger quantities of liquid. Such a facility requires high power electron beam machines, which typically have greatly reduced specific capital equipment costs expressed in $/watt.

The cost to treat 1 liter of liquid is comprised of three components: the energy cost, the capital cost and the maintenance cost. The energy cost is determined by the required dose to achieve a certain kill ratio. For a typical dose of 100 krad (1 kilogray), it is necessary to treat each gram of water with 1 Joule of E-beam energy. Therefore, to treat 1 liter of water an energy of 1 kJ or 2.78 E-4 kWh is required. If one further considers the efficiency of energy input to energy delivered to the liquid, one arrives at an energy requirement in the vicinity of 5 E-4 kWh. If one then assumes an energy cost of 8 cents per kWh, one obtains an energy cost per liter of 4 E-5 $/liter.

The capital costs vary greatly with the size of the installation. For example, a 10 kW installation might have specific costs of 50$/W, while a 1 MW installation would have specific costs of only $5/W. A 10 kW installation is capable of treating 20,000 l/hr or 138 million liters per year, assuming a utilization factor of 80%. For an equipment cost of $500,000, and assuming 12% for interest and depreciation one arrives at a yearly capital cost of $60,000 or at a specific cost of 4.35 E-4 $/l. The specific capital costs for a 1 MW installation are, on the other hand, only 4.35 E-5 $/l. This show that for small installations, the energy and capital costs are approximately equal, while for large installations the energy costs dominate.

The specific maintenance costs are again much higher for a small installation, as both installations require the need of one well trained technical person.

In addition to the foregoing economic considerations, considerations of energy loss by an electron beam passing through the atmosphere also favor high beam currents. An electron beam emerging into the atmosphere loses energy by collisions with air molecules but, in turn, also heats the gas it encounters. A high current beam will heat the gas more than a low current beam, thus it will more strongly reduce the air density and suffer, percentage-wise, less energy loss than a low current beam. Furthermore, the high current beam will spread less as it travels in lower density gas. An analysis of this phenomenon in some detail is presented in a paper by S. Philp entitled "Heating of the Air by the E-beam and its Effect on Energy Loss and Scattering", a copy of which has been designated "Exhibit A" and is filed with this application.

For processes other than the foregoing high-volume processes, such as the treatment of "hazardous waste" such as chemical waste, the required exposure is higher and therefore the throughput will be less. One purpose in this connection is to break up solvents in the hazardous waste, such as carbon tetrachloride. A dose of about a megarad is required, but there is no flow limitation.

SUMMARY OF THE INVENTION

The present invention deals with the scanning or sweeping mechanism for the electron beam and imparts a tubular or circular flow to the liquid material to be irradiated while imparting a rotary motion to the electron beam, so that the point of intersection between the electron beam and the sheet of liquid material repeatedly moves around a circle through which the material passes.

Of course, the greater the radius of this circle the larger the volume which can be irradiated for a given velocity of the liquid. The limitation on this length is the path-length in air, typically of the order of one meter; long path-lengths in air result in excessive energy loss. If the beam is scanned linearly in air, a limitation on the amplitude of the scan is imposed by the increasing angle at which the beam strikes the liquid material, thereby reducing penetration. This typically limits the scanning angle to about 30 degrees. If the beam path in air is one meter, the scan length is thus one meter. However, by the circular scan of the invention, the length of the intersection between the electron beam and the material is $2\pi$ meters; this is approximately a sixfold increase in the volume of water treated at a given water velocity.

BRIEF DESCRIPTION OF THE DRAWINGS

The invention may best be understood from the following detailed description thereof, having reference to the accompanying drawings, in which:

FIG. 4 is a diagrammatic sketch showing an alternate drive system for rotation of the magnet of FIG. 1 or 2, FIG. 5 is a diagrammatic sketch showing a still another drive system for rotation of the magnet of FIG. 1 or 2.

DESCRIPTION OF THE PREFERRED EMBODIMENT

Figure 1:
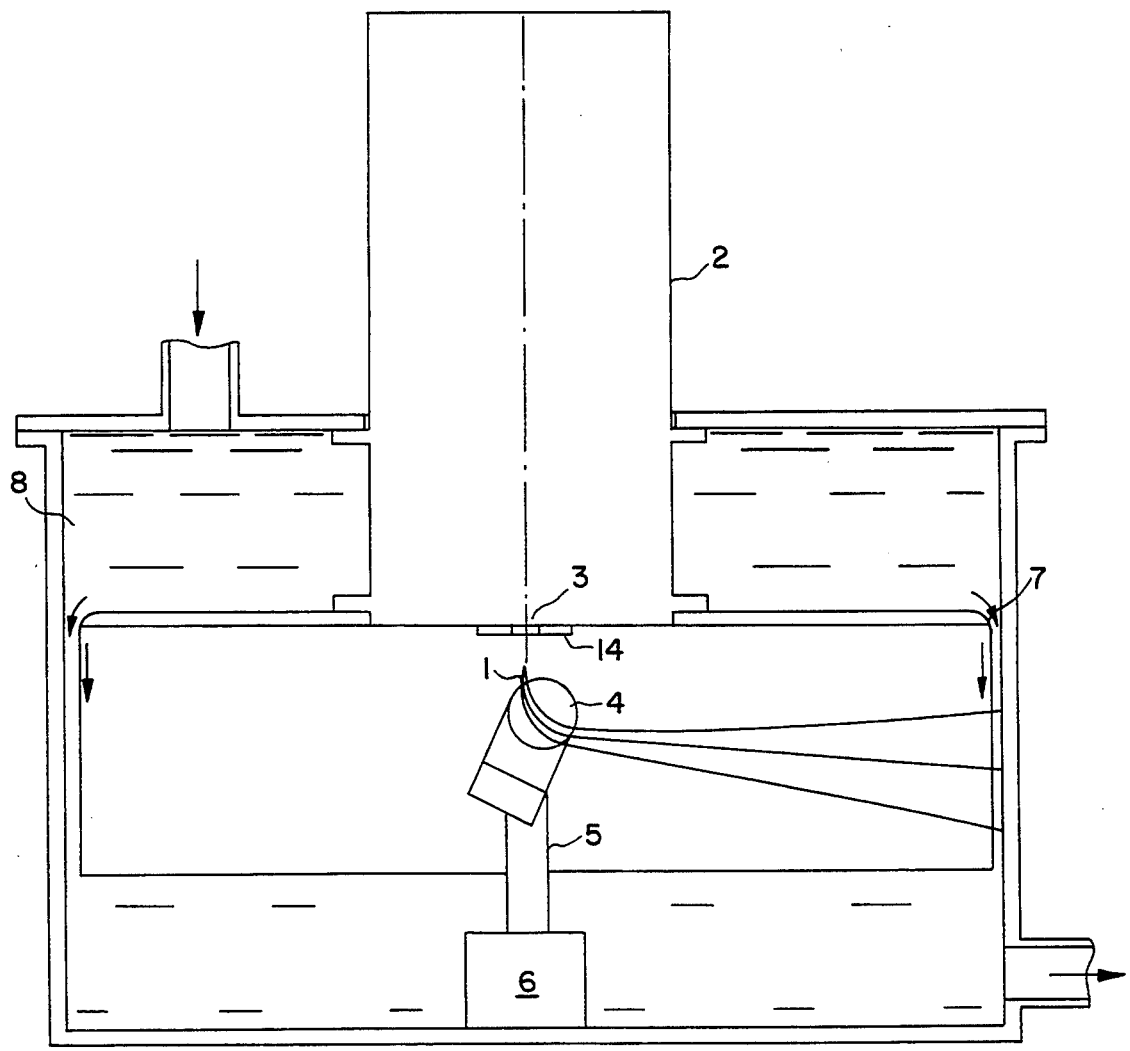
FIG. 1 is a central section through one embodiment of electron irradiation apparatus with vertical water flow suitable for carrying out the method of the invention.

Referring now to FIG. 1, in the embodiment of the invention therein shown an electron beam 1 is produced in a vertical direction by means of an accelerator 2, and the vertical electron beam 1 emerges from the accelerator 2 through an orifice 3 and passes between the pole pieces of a magnet 4 excited with permanent magnet material or by conventional current-carrying coils. The magnetic field required for bending 2-MeV electrons through an arc with radius 8 centimeters is approximately 0.1 Tesla (1 kilogauss), and so only a relatively small amount of permanent-magnet material is required.

Because the beam expands rapidly once it has emerged into air of atmospheric pressure, it is necessary that the airgap of the magnet be relatively large. It may also be advisable to protect the pole surfaces of the magnet with a more refractory material, such as tantalum sheets. The magnet shown in FIG. 1 deflects the beam from a vertical direction to a direction that is closer to horizontal. The magnet is mounted on a vertical shaft 5 which rotates rapidly, for instance by being driven by an electric motor 6 as shown in the figure. The beam is thus swept in a circle, and hence, in the case shown in FIG. 1, can treat a cylindrical stream of water emerging from a slim, substantially circular, opening 7, as shown. The flow rate is regulated by monitoring the pressure in the inlet chamber 8.

The diameter of the orifice 3 may be about 3 millimeters, and this orifice 3 must be shielded from the magnetic field because there must be no deflection field in the orifice 3. This shielding can be accomplished by placing a circular ferrite disc 14 with a central hole of, for instance, 5mm diameter under orifice 3.

Figure 2:
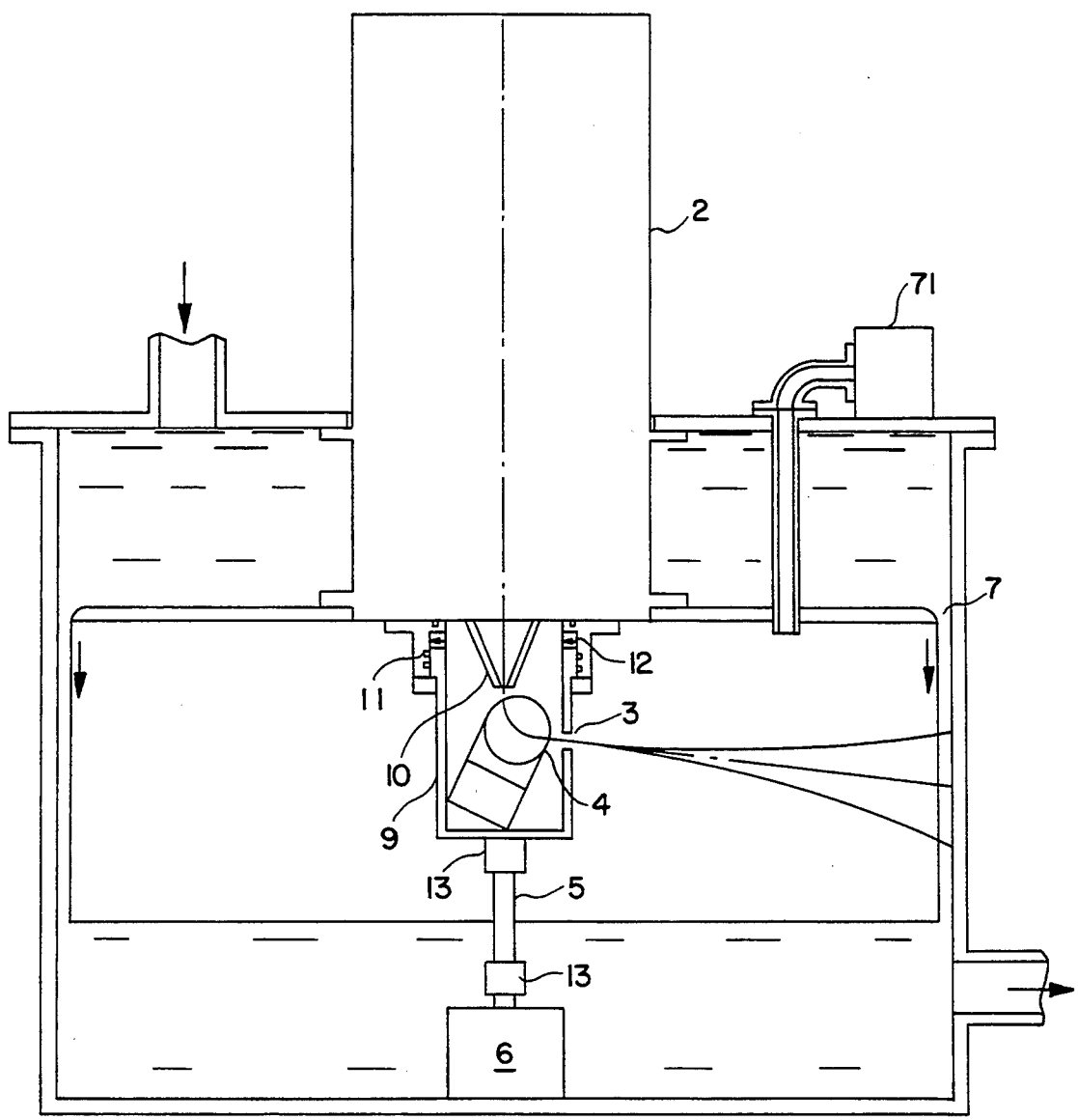
FIG. 2 is a view, similar to that of FIG. 1, showing a modification of the embodiment of FIG. 1.

An alternative embodiment of the invention is shown in FIG. 2. Referring thereto, the sweep magnet 4 can alternatively be mounted in a rotating chamber 9 which is connected to a fore-vacuum pump through the accelerator enclosure 2. A conical nozzle 10 is part of a chamber representing the second stage of vacuum pumpout. One or more rotating vacuum seals 11 are provided, but these do not have to be 100% leakproof since a major leak through the orifice 3 can not be avoided and will dominate the air flow. A ball-race 12 is provided, and it has to withstand the vertical component of the air pressure on the rotating chamber 9. The drive shaft 5 has to have flexible couplings 13 because of unavoidable misalignments between the motor axis and cylinder axis.

If one compares the circular sweep mechanisms of the present invention, as hereinbefore described with reference to either FIG. 1 or FIG. 2, with a line scanner placed outside the last orifice, it may be seen that the circular sweep of the invention has the following advantages over the line scanner:

1. The circular sweep mechanism is much simpler than a sweep magnet and electronic driver.
2. It is practical to make a much longer sweep, because the length of the linear sweep would, for practical reasons such as path length in air and angle of incidence, be comparable to the radius of circle traced by the circular sweep mechanism, whereas the length of the circular sweep mechanism is the circumference of that circle.
3. There are no "end effects" with reduced beam penetration, such as accompany the line sweep because of non-normal angle of incidence.

The system of the present invention as shown in either FIG. 1 or FIG. 2 is closed, and this has several implications, as follows:

1. The steel tank is the first barrier for radiation protection.
2. Ozone produced by the electron beam is not released in large quantities to the atmosphere but is given a chance to react with contaminants in the water.
3. It is possible, if desired, to evacuate the containment chamber, for instance by aid of one or more vacuum pumps 71 (e.g. water jet pumps), to approximately 20 Torr (the vapor pressure of water at room temperature). This means less loss in beam energy to the air, less beam broadening, and less ozone production. The air load on the pump or pumps is only the air brought into the chamber by the water. The treated water must be pumped out of the chamber against air pressure.

The present invention also includes a system with rotational scanning, as described hereinabove, in which the sweep magnet is inside the main vacuum system and the beam exits through a cylindrical thin window. If the beam is of high intensity, some arrangement must be made to enlarge the spot size on the window.

Effluent gases from power plants, smelters, etc. can also be treated with an electron beam in a system fundamentally similar to the one hereinbefore described, although in many cases gas scattering produces enough spreading of the beam in these applications. Lower electron energy is needed for such systems. Therefore, the accelerator is smaller and could, in principle, be placed in the middle of a smokestack. Alternatively, the electron beam can be piped in through a vacuum system with, perhaps, the first two stages of differential pumping close to the last orifice. It may also be advisable to flush the last orifice with a clean gas to prevent too much contamination of vacuum pumps. Clean gas flushing (with helium) is utilized in electron-beam welders, but mostly for another reason: to reduce the scattering and thereby keep the beam diameter small.

Figure 3:
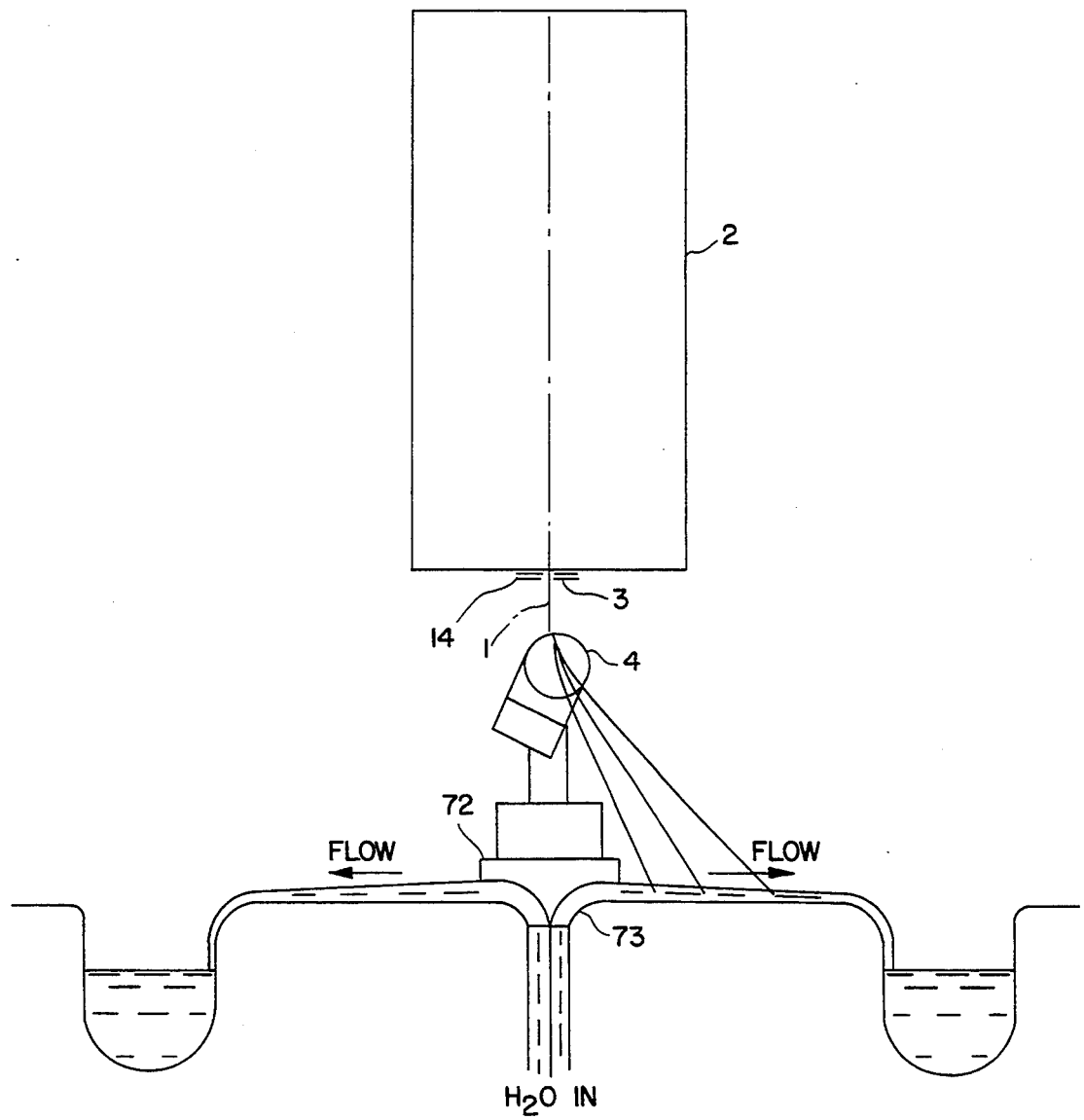
FIG. 3 is a central section of an irradiation apparatus with horizontal water flow, representing another embodiment of the invention.

Referring now to FIG. 3, in the structure therein shown the electron beam is deflected by a rotating magnet through an angle of 30 degrees, so that rotation of the magnet causes the electron beam to intersect the material irradiated in an annulus having a width determined by the scattering of the electron beam. Water is conveyed vertically upward along the extended axis of the electron beam, and then directed outwardly in a circular pattern into a suitable circular moat for temporary accumulation. The water is thus conveyed in a vertical conduit along said axis, said conduit terminating in a baffle 72 supported by radial fins 73 between which said liquid passes outwardly in a circular pattern.

Referring now to FIG. 4, the permanent magnet of FIGS. 1 or 2 could be supported from the baseplate of the generator, instead of from the foot of the tank. The motor for the permanent magnets could have a hollow shaft through which the electron beam could travel. The motor could be air driven, and thus be less susceptible to radiation damage.

Referring now to FIG. 5, the motor could be connected to the rotating permanent magnets via drive shafts. This arrangement has the advantage, that the motor is outside the ozone atmosphere and is also protected from extreme radiation. Also the distance between the beam exit and the permanent magnets could be made short, thus reducing the effects of beam spread and scatter.

Figure 6:
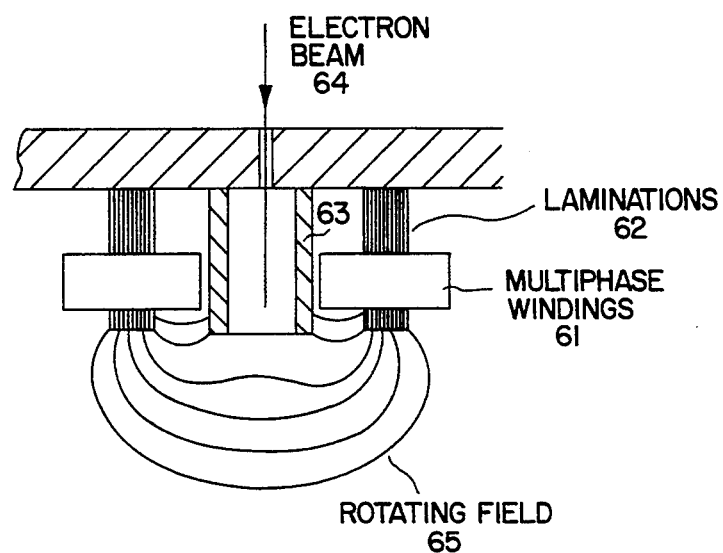
FIG. 6 is a vertical central section showing another manner of rotating a magnetic field in which multiphase windings are employed to rotate the magnetic field in a similar manner as in an electric motor.
Figure 7:
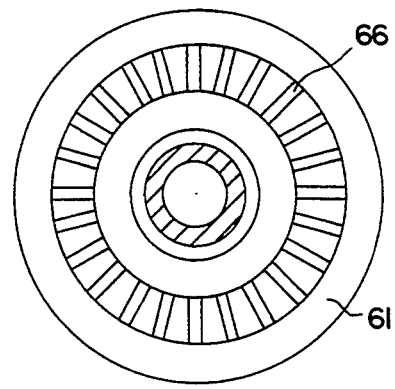
FIG. 7 is a section along the line 7—7 of FIG. 6.
Figure 8:
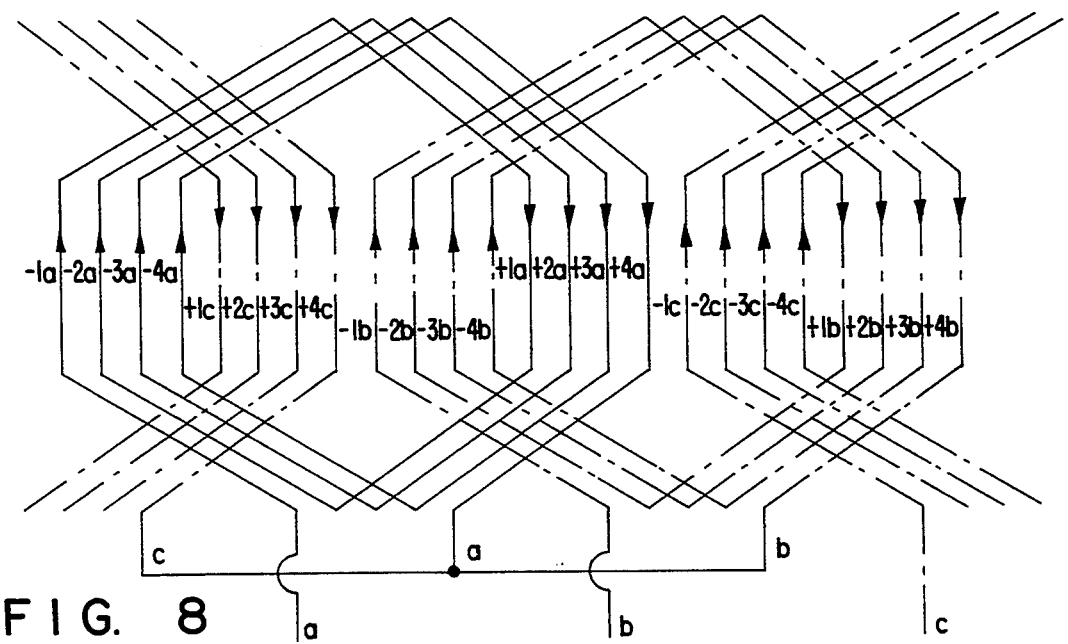
FIG. 8 is a simplified folded-out diagram of suitable windings for the magnet of FIGS. 6 and 7.

Referring now to FIGS. 6, 7, and 8, one could create a rotating magnetic field by aid of multiphase windings 61 (field coils) as is commonly done in rotating electric machinery and well known to those skilled in the art. The multiphase windings 61 are mounted on cores 62 having laminations in the direction shown. The advantage of this arrangement would be no rotating parts and that it may be easier to keep the system protected from the corrosive action of a chemically active atmosphere.

In using a rotating magnetic field produced by multiphase windings to sweep the beam in a circle or cone, a problem is that the magnetic field starts bending the electrons too early, before they are out of the cylindrical gap. So one needs some shielding of the field. As shown in FIGS. 6 and 7, a ferrite tube 63 may be used for this purpose. Laminations are not suitable because the direction of the field is not that well defined; the result will be eddy-currents and heating. A copper shield is not effective enough at 60 cycles and even worse for lower frequencies.

In FIGS. 6 and 7 the electron beam is shown at 64, the rotating field is shown at 65, and the slots for the windings are shown at 66.

FIG. 8 shows a folded-out diagram of windings in three-phase star connection that will produce the rotating field in the magnet of FIGS. 6 and 7. For simplicity, the diagram shows only one conductor per slot. In practice, to keep the impedance at a suitable high level, there will be multiple turns.

FIGS. 7 and 8 are shown here with 24 slots and 24 conductors, respectively, energized from a three-phase line. This choice is meant as an example, only. As is well known to those skilled in the art, there are many ways of producing a rotating magnetic field, by using two-, three- or multi-phase currents directly from power lines or from electronic sources.

Having thus described the principles of the invention, together with illustrative embodiments thereof, it is to be understood that although specific terms are employed, they are used in a generic and descriptive sense, and not for purposes of limitation, the scope of the invention being set forth in the following claims.

I claim:

1. Apparatus for irradiating a liquid with electrons, comprising in combination:

a chamber for accumulating liquid to be irradiated, said chamber including a circular exit opening through which said liquid flows in the form of a tubular sheet having an axis as a result of the liquid pressure within said chamber, an electron accelerator adapted to direct an electron beam along said axis, said electron accelerator including an evacuated region terminating in a small orifice for passage of said electron beam into the region bounded by said tubular sheet, a pair of magnetic pole faces flanking said electron beam in said region and adapted to deflect said electron beam onto said tubular sheet, and means for rotating said pair of magnetic pole faces about said axis to scan circularly said electron beam onto said tubular sheet.

2. Apparatus in accordance with claim 2, further comprising a magnetic shield with a central hole is placed adjacent said orifice, said central hole being in substantial alignment with said orifice.

3. Apparatus in accordance with claim 1, wherein the radius of said tubular sheet is of the order of one meter and wherein the liquid is moved at high velocity consistent with avoiding non-uniform irradiation.

4. Apparatus in accordance with claim 1, wherein the pressure in the portion of said chamber into which said liquid flows after passage through said circular exit opening is reduced by use of one or more vacuum pumps.

5. Apparatus for irradiating a liquid with electrons, comprising in combination:

a chamber for accumulating liquid to be irradiated, said chamber including a circular exit opening through which said liquid flows in the form of a tubular sheet having an axis as a result of the liquid pressure within said chamber, an electron accelerator adapted to direct an electron beam along said axis, said electron accelerator including an evacuated region terminating in a small orifice for passage of said electron beam into the region bounded by said tubular sheet, a plurality of field coils flanking said electron beam in said region and adapted to deflect said electron beam onto said tubular sheet, and means for energizing said field coils with alternating current in such a manner that the phase of the current in each field coil differs from that in other field coils so as to rotate the field produced by said field coils about said axis to scan circularly said electron beam onto said tubular sheet.

6. Apparatus in accordance with claim 5, further including a ferrite tube within said plurality of field coils and about said electron beam.

7. Apparatus in accordance with claim 5, wherein the radius of said tubular sheet is of the order of one meter and wherein the liquid is moved at high velocity consistent with avoiding non-uniform irradiation.

8. Apparatus in accordance with claim 5, wherein the pressure in the portion of said chamber into which said liquid flows after passage through said circular exit opening is reduced by use of one or more vacuum pumps.

9. Apparatus for irradiating a liquid with electrons, comprising in combination:

a chamber for accumulating liquid to be irradiated, said chamber including a vertical conduit for said liquid having an axis and terminating in a baffle supported by radial fins between which said liquid passes outwardly in a circular pattern, an electron accelerator adapted to direct an electron beam along said axis towards said baffle, said electron accelerator including an evacuated region terminating in a small orifice for passage of said electron beam into said chamber, a pair of magnetic pole faces flanking said electron beam in said region and adapted to deflect said electron beam onto said circular pattern, and means for rotating said pair of magnetic pole faces about said axis to scan circularly said electron beam onto said circular pattern.

10. Apparatus in accordance with claim 9, further comprising a magnetic shield with a hole is placed adjacent said orifice, said hole being in substantial alignment with said orifice for passage of said beam therethrough.

11. Apparatus for irradiating a liquid with electrons, comprising in combination:

a chamber for accumulating liquid to be irradiated, said chamber including a vertical conduit for said liquid having an axis and terminating in a baffle supported by radial fins between which said liquid passes outwardly in a circular pattern, an electron accelerator adapted to direct an electron beam along said axis towards said baffle, said electron accelerator including an evacuated region terminating in a small orifice for passage of said electron beam into said chamber, a plurality of field coils flanking said electron beam in said region and adapted to deflect said electron beam onto said circular pattern, and means for energizing said field coils with alternating current in such a manner that the phase of the current in each field coil differs from that in other field coils so as to rotate the field produced by said field coils about said axis to scan circularly said electron beam onto said circular pattern.

12. Apparatus in accordance with claim 11, further including a ferrite tube within said plurality of field coils and about said electron beam.

* * * * *